(12) United States Patent
Fukutani et al.

(10) Patent No.: US 9,131,851 B2
(45) Date of Patent: Sep. 15, 2015

(54) BIOLOGICAL INFORMATION IMAGING APPARATUS AND METHOD FOR ANALYZING BIOLOGICAL INFORMATION

(75) Inventors: Kazuhiko Fukutani, Yokohama (JP); Takao Nakajima, Ebina (JP); Yasufumi Asao, Atsugi (JP)

(73) Assignee: Canon Kabushiki Kaisha, Tokyo (JP)

( * ) Notice: Subject to any disclaimer, the term of this patent is extended or adjusted under 35 U.S.C. 154(b) by 1337 days.

(21) Appl. No.: 12/365,237

(22) Filed: Feb. 4, 2009

(65) Prior Publication Data

US 2009/0198128 A1 Aug. 6, 2009

(30) Foreign Application Priority Data

Feb. 6, 2008 (JP) ................................. 2008-026067

(51) Int. Cl.
  *A61B 5/00* (2006.01)
  *G01N 29/24* (2006.01)
  *A61B 8/08* (2006.01)

(52) U.S. Cl.
  CPC ............. *A61B 5/0095* (2013.01); *A61B 5/0091* (2013.01); *A61B 5/4312* (2013.01); *A61B 8/0825* (2013.01); *A61B 5/489* (2013.01); *A61B 5/4887* (2013.01); *A61B 8/5223* (2013.01); *G01N 29/2418* (2013.01)

(58) Field of Classification Search
  CPC .. A61B 5/0091; A61B 5/0095; A61B 5/4312; A61B 5/4887; A61B 5/489; A61B 8/0825; A61B 8/5223; G01N 29/2418
  USPC .................................. 600/407, 437, 438, 476
  See application file for complete search history.

(56) References Cited

U.S. PATENT DOCUMENTS

| | | | | |
|---|---|---|---|---|
| 5,348,002 A | * | 9/1994 | Caro | 600/310 |
| 5,840,023 A | * | 11/1998 | Oraevsky et al. | 600/407 |
| 6,002,958 A | * | 12/1999 | Godik | 600/407 |
| 6,041,248 A | * | 3/2000 | Wang | 600/407 |
| 6,212,421 B1 | | 4/2001 | Vo-Dinh et al. | 600/407 |
| 6,390,978 B1 | * | 5/2002 | Irion et al. | 600/437 |

(Continued)

FOREIGN PATENT DOCUMENTS

JP 2005-021380 1/2005

OTHER PUBLICATIONS

Mobley et al., "Photoacoustic method for the simultaneous acquisition of optical and ultrasonic spectra", Acoustics Research Letters Online, Jul. 2003, pp. 89-94.*

*Primary Examiner* — Katherine Fernandez
(74) *Attorney, Agent, or Firm* — Fitzpatrick, Cella, Harper & Scinto

(57) ABSTRACT

There are provided a biological information imaging apparatus that can measure ultrasound generated from an optical absorber in a deep part of a subject living body with high sensitivity, and a method for analyzing biological information using the biological information imaging apparatus. The biological information imaging apparatus that detects ultrasound and images biological information, includes: a light source that irradiates the subject with light for generating ultrasound from an optical absorber existing in the subject; an ultrasound transmission unit that transmits focused ultrasound to a specific region where the optical absorber exists; and an ultrasound detection unit that detects an ultrasound synthesized signal due to interaction between ultrasound generated from the optical absorber that absorbs the light and the focused ultrasound transmitted to the specific region.

18 Claims, 6 Drawing Sheets

(56) References Cited

U.S. PATENT DOCUMENTS

| | | | |
|---|---|---|---|
| 6,633,774 B2* | 10/2003 | Kruger | 600/407 |
| 6,662,040 B1* | 12/2003 | Henrichs et al. | 600/431 |
| 6,846,288 B2* | 1/2005 | Nagar et al. | 600/437 |
| 6,979,292 B2* | 12/2005 | Kanayama et al. | 600/437 |
| 7,541,602 B2* | 6/2009 | Metzger et al. | 250/494.1 |
| 7,665,364 B2* | 2/2010 | Su et al. | 73/643 |
| 7,740,585 B2* | 6/2010 | Oraevsky et al. | 600/443 |
| 7,747,301 B2* | 6/2010 | Cheng et al. | 600/322 |
| 8,103,329 B2* | 1/2012 | Fomitchov et al. | 600/407 |
| 2005/0004458 A1 | 1/2005 | Kanayama et al. | 600/437 |
| 2007/0093707 A1* | 4/2007 | Noguchi | 600/390 |
| 2007/0220978 A1* | 9/2007 | Su et al. | 73/632 |
| 2008/0181851 A1* | 7/2008 | Guccione | 424/9.5 |
| 2008/0306371 A1 | 12/2008 | Fukutani et al. | 600/407 |
| 2009/0002685 A1 | 1/2009 | Fukutani et al. | 356/72 |

\* cited by examiner

BIOLOGICAL INFORMATION IMAGING APPARATUS AND METHOD FOR ANALYZING BIOLOGICAL INFORMATION

BACKGROUND OF THE INVENTION

1. Field of the Invention

The present invention relates to a biological information imaging apparatus and a method for analyzing biological information.

2. Description of the Related Art

Imaging apparatuses using X-ray (mammography), ultrasound or MRI (magnetic resonance imaging) have been often used for diagnosing breast cancer.

In recent years, a photoacoustic imaging apparatus has been noted, in which the imaging apparatus propagates pulsed light from a light source such as a laser into a living body, detects a photoacoustic signal generated by absorption of the propagated light into the living body, and images an initial pressure distribution or absorption coefficient distribution in the living body. This technique is referred to as PAT (PhotoAcoustic Tomography).

Generally, photoacoustic tomography has the following advantages. First, photoacoustic tomography can perform functional imaging of oxygen metabolism and brain activity without having to perform imaging of a living body using X-rays, ultrasound or MRI.

For example, oxy-hemoglobin and deoxy-hemoglobin have different optical absorption spectrums. Thus, a plurality of wavelengths can be used to measure the absorption spectrums to measure oxygen saturation in blood and oxygen metabolism.

The imaging of oxygen metabolism advantageously enables examination of cancerous tumors, or of active areas in the brain.

Imaging of oxygen metabolism also enables identification of the composition of a diseased part from the absorption spectra.

Second, light does not involve radiation exposure unlike X-rays or radiation such as gamma-rays, and enables repeated non-invasive diagnosis.

Third, medical devices can be reduced in size and cost as compared with MRI and PET (positron emission tomography) apparatus.

As compared with an optical diffusion imaging apparatus also capable of functional imaging that detects diffused light and images the inside of a living body, lower scattering of photoacoustic waves occurs in the living body, which thus enables an increase in resolution.

In recent years, Japanese Patent Application Laid-open No. 2005-021380 proposes an apparatus including a combination of an ultrasound diagnostic apparatus and a photoacoustic imaging apparatus for using both an ultrasound echo image and a photoacoustic image for diagnosis.

In this apparatus, by the combination of the apparatuses and partial sharing of systems, both of the photographed images can be displayed without distortion.

In the general photoacoustic imaging apparatus, strong optical diffusion in the subject living body causes a significant reduction in light intensity as the light penetrates into deeper parts of the living body. Specifically, in the deep parts of the living body, the number of photons reaching the optical absorber is significantly decreasing.

Thus, a photoacoustic signal that can be observed by a sound wave detector placed on a surface of the living body cannot be obtained from the deep part of the subject, and the region in the living body that can be imaged is limited.

Such a problem is not disclosed in the combination of the ultrasound apparatus and the photoacoustic imaging apparatus in Japanese Patent Application Laid-open No. 2005-021380.

SUMMARY OF THE INVENTION

In view of the above problem, the present invention has as an object to provide a biological information imaging apparatus that can measure ultrasound generated from an optical absorber in a deep part of a subject living body with high sensitivity, and a method for analyzing biological information using the biological information imaging apparatus.

The present invention provides a biological information imaging apparatus configured as described below, and a method for analyzing biological information with a signal obtained from the apparatus.

The present invention provides a biological information imaging apparatus that detects ultrasound and images biological information, including: a light source that irradiates a subject with light for generating ultrasound from an optical absorber existing inside the subject; an ultrasound transmission unit that transmits focused ultrasound to a specific region where the optical absorber exists; and an ultrasound detection unit that detects an ultrasound synthesized signal due to interaction between ultrasound generated from the optical absorber that absorbs the light and the focused ultrasound transmitted to the specific region.

In one aspect of the present invention, a method for analyzing biological information that uses the biological information imaging apparatus to determine optical characteristic value distribution in a subject, includes: a first step of analyzing an ultrasound synthesized signal due to the interaction detected by an ultrasound detection unit to obtain information on optical energy absorption density in a specific region; and a second step of scanning other regions in the subject with focused ultrasound and repeating the first step to image the information on optical energy absorption density distribution in a living body.

In another aspect of the present invention, a method for analyzing biological information that uses the biological information imaging apparatus to determine optical characteristic value distribution in a subject, includes: irradiating the subject with light and irradiating the subject with first ultrasound focused into a specific region in the subject simultaneously; receiving third ultrasound due to interaction between second ultrasound generated when an optical absorber in the specific region absorbs the light and the first ultrasound emitted to the specific region; and calculating an optical characteristic value of the specific region from the received third ultrasound.

The present invention can realize a biological information imaging apparatus that can measure the ultrasound generated from the optical absorber in the deep part of the subject living body with high sensitivity, and can increase an imaging range of biological information, and a method for analyzing biological information using the biological information imaging apparatus.

Further features of the present invention will become apparent from the following description of exemplary embodiments with reference to the attached drawings.

DESCRIPTION OF THE EMBODIMENTS

Preferred embodiments of the present invention will now be described in detail in accordance with the accompanying drawings.

Embodiment 1

First, a biological information imaging apparatus according to Embodiment 1 of the present invention will be described.

Figure 1:
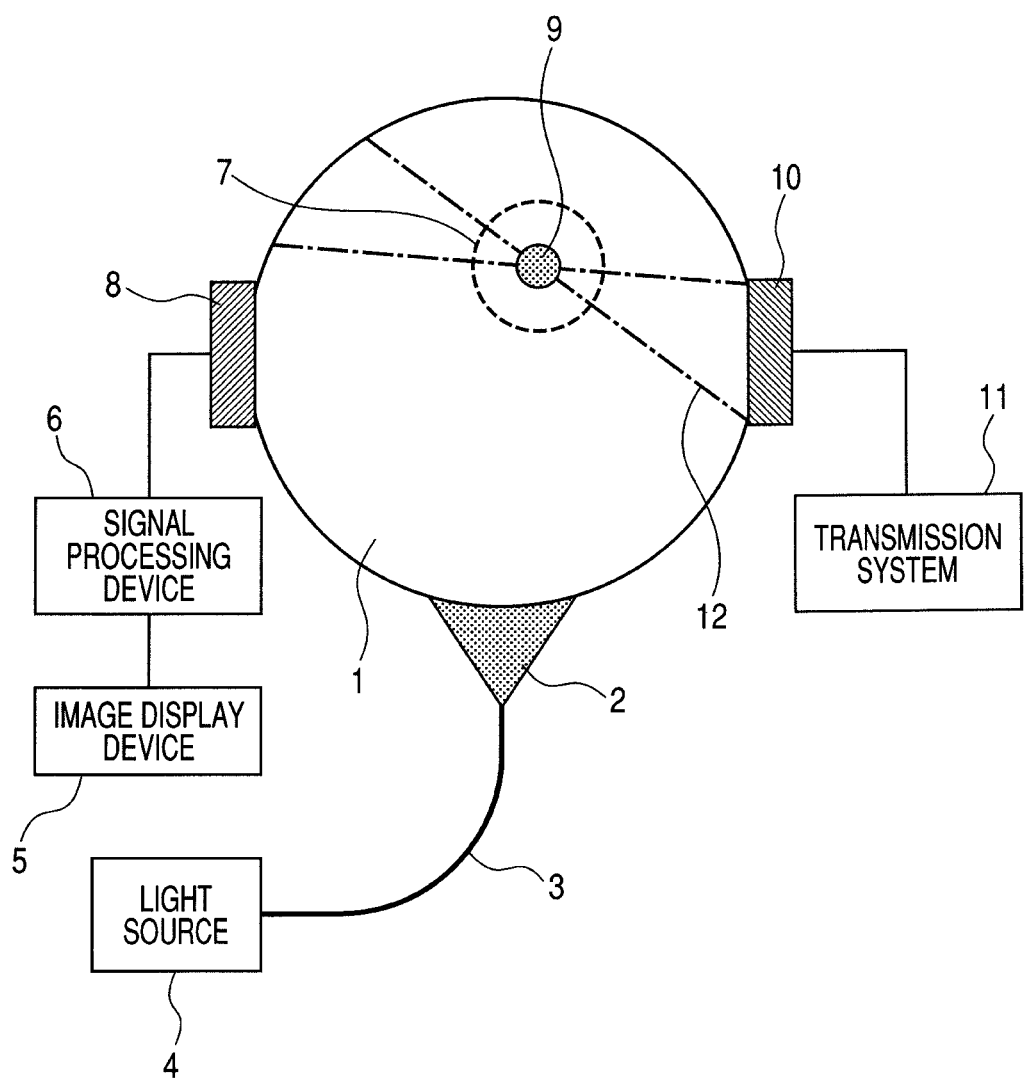
FIG. 1 illustrates an exemplary construction of a biological information imaging apparatus according to Embodiment 1 of the present invention.

FIG. 1 illustrates an exemplary construction of a biological information imaging apparatus according to the embodiment.

In FIG. 1, reference numeral 1 denotes a living body as a subject, 2; pulsed light, 3; an optical waveguide, 4; a light source, 5; an image display device, 6; a signal processing device, and 7; ultrasound generated from an optical absorber (sometimes referred to herein as "second ultrasound").

Reference numeral 8 denotes an ultrasound detector (ultrasound detection unit), 9; an optical absorber, 10; an ultrasound transmission device (ultrasound transmission unit), 11; an ultrasound transmission control system, and 12; focused ultrasound (sometimes referred to herein as "first ultrasound").

The biological information imaging apparatus of the embodiment can image information as described below for diagnosing tumor or vascular diseases and follow-up of chemotherapy.

Specifically, the biological information imaging apparatus can image information on optical characteristic value distribution, particularly, optical absorption coefficient distribution in the living body, and information on concentration distribution or composition of substances that constitute living tissue, obtained from the above described information.

Particularly, the biological information imaging apparatus is used in an apparatus for displaying images used for diagnosing breast cancer.

The biological information imaging apparatus of the embodiment includes a light source 4 that irradiates a subject living body 1 with pulsed light 2. The light from the light source 4 and directed at the living body 1 is mainly absorbed by an optical absorber 9, and temperature of the optical absorber 9 rapidly changes according to an amount of absorbed optical energy during the irradiation. Thermal expansion due to the rapid temperature change causes a pressure difference between the optical absorber 9 and its surroundings to generate ultrasound 7. The ultrasound 7 ("second ultrasound") generated from the optical absorber 9 that absorbs the light is sometimes referred to as photoacoustic waves.

The term "living body" herein refers to any part of a human body such as a breast, finger, foot or neck.

Generally, the pulsed light is generated from the light source 4 and directed to a surface of the living body through a light waveguide 3 such as an optical fiber or a liquid light guide. However, when energy of the pulsed light exceeds a limit of an optical propagation path such as an optical fiber, the pulsed light can be directed at the living body using a mirror or a lens without an optical guide.

The pulsed light can be diverged to some extent rather than converged for reducing irradiation energy incident per unit area on the surface of the living body.

Typically, an exposed area of the pulsed light is several square centimeters, but the area is set to an appropriate value according to the energy of the pulsed light and a maximum permissible exposure to the living body.

The biological information imaging apparatus of the embodiment includes an ultrasound transmission device 10 that can focus ultrasound ("first ultrasound") into a specific region in the subject living body by a known method.

Generally, the ultrasound transmission device includes a plurality of ultrasound generation elements that can generate ultrasound.

The ultrasound transmission device can include a plurality of ultrasound generation elements arranged in the form of an array, for example, a two-dimensional array in order to transmit focused ultrasound to various regions. A one-dimensional linear array and an acoustic lens can provide the same advantage. As the elements that generate ultrasound, piezoelectric or capacitance transducers can be used.

In use of the ultrasound generation elements arranged in the form of the two-dimensional array, the generated ultrasound can be electronically controlled so as to have an energy density peak in the specific region in the living body. The ultrasound transmission device 10 is controlled by a transmission signal processing system that generates a signal for focusing ultrasound into the specific region.

The ultrasound transmission device 10 can be controlled by a computer. In an illustrated example, sound wave is focused into a region where the optical absorber 9 exists in the living body, but the ultrasound can be focused into any locations.

Further, the biological information imaging apparatus of the embodiment includes an ultrasound detector (ultrasound detection unit) 8. A tumor, vessel or other optical absorber 9 in the living body absorbs a part of energy of the light to generate ultrasound 7, and the ultrasound detector 8 detects the ultrasound 7 and converts the ultrasound into an electric signal.

Generally, the ultrasound detector 8 can also include a plurality of ultrasound detection elements. The ultrasound detector 8 can include ultrasound detection elements arranged two-dimensionally, for example, in the form of a two-dimensional array for obtaining three-dimensional image information. As the ultrasound detection elements, piezoelectric, capacitance, or light detecting transducers can be used.

The ultrasound detector 8 can also detect reflection of the focused ultrasound 12 or transmission ultrasound.

The ultrasound detector 8 can simultaneously detect the ultrasound 7 generated from the optical absorber 9 in the living body that absorbs a part of the energy of the light, and the reflection of the focused ultrasound 12 or the transmission ultrasound.

The biological information imaging apparatus also includes a signal processing device 6 that analyzes the electric signal obtained by the ultrasound detector 8, and an image display device 5 that displays an image based on a processed signal.

The signal processing device 6 typically includes an amplifier that amplifies a detected ultrasound signal, an A/D converter that converts an analog signal into a digital signal, and an FPGA or a personal computer that performs a signal processing.

As the image display device 5, a display that displays an image signal generated by the computer is typically used. In the biological information imaging apparatus of the present invention, the image display device 5 has an arbitrary construction.

The biological information imaging apparatus of the embodiment includes the above-described components.

The light source 4 that irradiates the living body with the pulsed light is used as a unit for emitting light having a particular wavelength absorbed by a particular component among the components that constitute the living body.

The light source 4 can be a pulsed light source that can generate pulsed light on the order of several to several hundred nanoseconds for efficiently generating ultrasound from the optical absorber. Specifically, a time width of the pulsed light is from 100 picoseconds to 500 nanoseconds, and can be from 1 nanosecond to 100 nanoseconds. In this case, the pulsed light can have a wavelength of 400 nm to 1600 nm.

A laser can be used as the light source, or a light emitting diode can be used instead of a laser.

Various lasers can be used, including a solid-state laser, a gas laser, a dye laser, and a semiconductor laser.

In the present embodiment, each light source 4 can emit light having different wavelengths rather than light having a single wavelength for measuring differences of optical characteristic value distribution, particularly, optical absorption coefficient distribution according to the wavelengths.

In this case, the light source can be a laser using a dye, OPO (Optical Parametric Oscillators) or an optical crystal such as titanium sapphire and alexandrite that can convert the wavelength of emitted light.

The light source used can have a wavelength of 700 nm to 1100 nm with low absorption in the living body.

For determining an optical characteristic value distribution of living tissue relatively near the surface of the living body, a broader wavelength range than the above, for example, a wavelength range of 400 nm to 1600 nm, can be used.

The ultrasound detector 8 in the embodiment needs to detect the ultrasound 7 generated from the optical absorber 9 in the living body that absorbs a part of the energy of the light from the light source that is shone onto the living body, and convert the ultrasound into an electric signal.

Thus, a receivable frequency band of the ultrasound detector 8 is desirably optimized according to the size of the optical absorber in the living body.

As the ultrasound detector 8, any sound wave detector can be used that can detect acoustic wave signals, such as a transducer using a piezoelectric phenomenon, a transducer using resonance of light, or a transducer using changes in capacity.

For example, for receiving ultrasound generated from optical absorbers of various sizes, a transducer using changes in capacity having a broad detection frequency band, or a plurality of transducers having different detection bands can be used.

The embodiment describes the case where one ultrasound detector 8 is arranged near the surface of the living body, but not limited to this, a plurality of ultrasound detectors 8 can be arranged so as to detect ultrasound at a plurality of locations.

Since detecting ultrasound at a plurality of locations provides the same advantage as in arranging the plurality of ultrasound detectors 8, one ultrasound detector can be used to two-dimensionally scan the surface of the living body.

However, the two-dimensionally arranged ultrasound detectors enable simultaneous detection of ultrasound signals at various locations, and can reduce a measurement time as compared with the method of scanning with the ultrasound detector.

When the electric signal obtained from the ultrasound detector 8 is mild, signal intensity can be amplified by the amplifier in the signal processing device 6.

Between the ultrasound detector 8 or the ultrasound transmission device 10 and the living substance 1 to be measured, an acoustic impedance matching is desirably used to prevent reflection of ultrasound.

The signal processing device 6 in the embodiment can analyze the electric signal from the ultrasound detector, and thus can derive information on the optical characteristic value distribution, particularly, on the optical absorption characteristic value distribution of the living body.

For example, as illustrated in FIG. 1, the signal processing device 6 calculates an optical energy absorption density of the specific region where the ultrasound is focused into, or an optical characteristic value relating to the optical absorption coefficient, based on the electric signal obtained by the ultrasound detector 8.

The signal processing device 6 of any type can be used that can store sound pressure changes of the ultrasound, and convert the changes into data relating to the optical characteristic value with a calculation unit.

For example, a data collection system and a computer that can analyze data stored in the system can be used.

The image display device 5 needs only to display an image obtained by analyzing an ultrasound signal, and various devices such as a liquid crystal display can be used.

When the light source can generate light having a plurality of wavelengths, and irradiates the living body with light having the plurality of wavelengths, information on the optical characteristic value distribution in the living body can be calculated for each wavelength, and concentration distribution of substances that constitute the living body can be imaged based on the information.

For example, information on an absorption coefficient distribution can be calculated, and the value can be compared with wavelength dependence specific to the substances that constitute the living tissue (such as glucose, collagen and oxy- and deoxy-hemoglobin) to image the concentration distribution of the substances that constitute the living body.

With the biological information imaging apparatus in the embodiment, ultrasound generated from the optical absorber in the deep part of the living body can be detected on the surface of the living body, and information on the optical characteristic value of the living body in various regions can be imaged as compared with the conventional technique.

Next, a method for imaging the biological information with the signal obtained from the biological information imaging apparatus in the embodiment will be described.

With reference to FIGS. 1 and 2A to 2C, an example of a flowchart for imaging information on absorption coefficient distribution that is the optical characteristic value distribution in the living body used in the embodiment of the present invention will be described.

Figure 3:
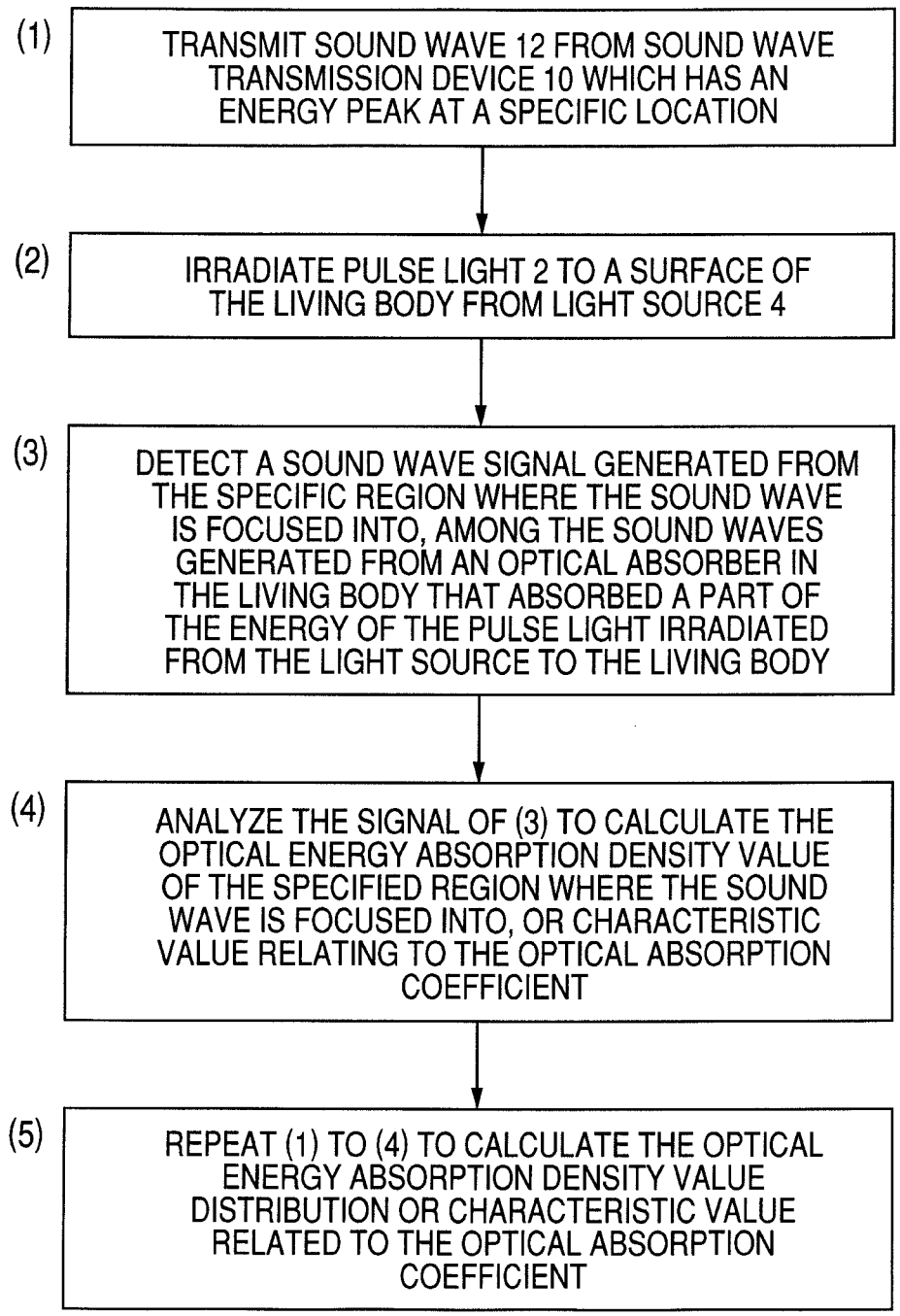
FIG. 3 illustrates an example of a flowchart for obtaining information on optical characteristic value distribution in a living body using the biological information imaging apparatus of the present invention.

The following items (1) to (5) correspond to the item numbers in the flowchart in FIG. 3, and will be described in the order.

(1) The ultrasound transmission device 10 transmits focused ultrasound 12 which has an energy peak at a specific location.

For example, a control signal is provided from an ultrasound transmission control system 11 to each ultrasound transmission element that constitutes the ultrasound transmission device 10, and ultrasound which has an energy peak in a specific region is generated and transmitted. For example, the specific region is irradiated with focused ultrasound having a waveform as in FIG. 2A.

Figure 2A:
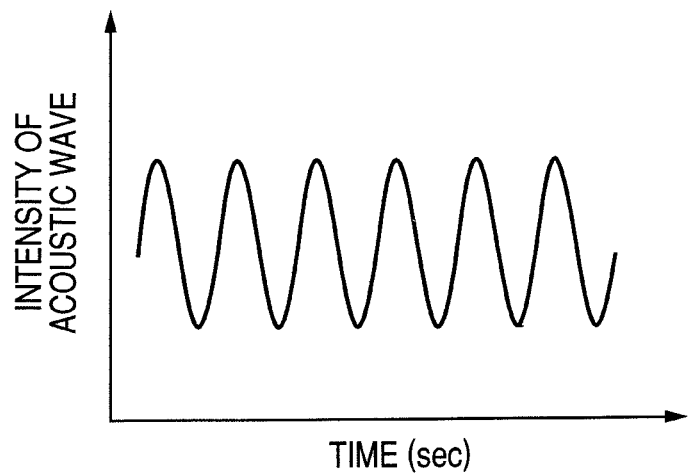
FIGS. 2A, 2B and 2C illustrate examples of ultrasound signals detected in the biological information imaging apparatus according to Embodiment 1 of the present invention.

In this case, the frequency of the sound wave in FIG. 2A can be about an inverse of a value obtained by dividing the size of the optical absorber in the specific region by sound speed, but the frequency can be continuously changed in a specific range. Details of the frequency of the focused ultrasound 12 will be described later.

FIG. 2A illustrates the waveform of the focused ultrasound having a single frequency, but not limited to this, various waveforms can be used. Specifically, the waveform of the ultrasound can have a plurality of frequencies after Fourier transform of the waveform rather than having a single frequency. The waveform of the ultrasound having a plurality of frequencies can be used to generate a waveform having a more similar shape to the waveform of the ultrasound generated by optical absorption.

(2) The pulsed light 2 is emitted from the light source 4 to the surface of the living body. Light exposure time is referred in a measurement period of the sound pressure changes. In the exposure with the focused ultrasound 12 in (1), the phase is adjusted with reference to the time.

(3) Ultrasound detector 8 detects ultrasound generated from the specific region where the sound wave is focused into, among the ultrasound generated from the optical absorber in the living body that absorbs a part of the energy of the pulsed light from the light source to the living body.

Figure 2B:
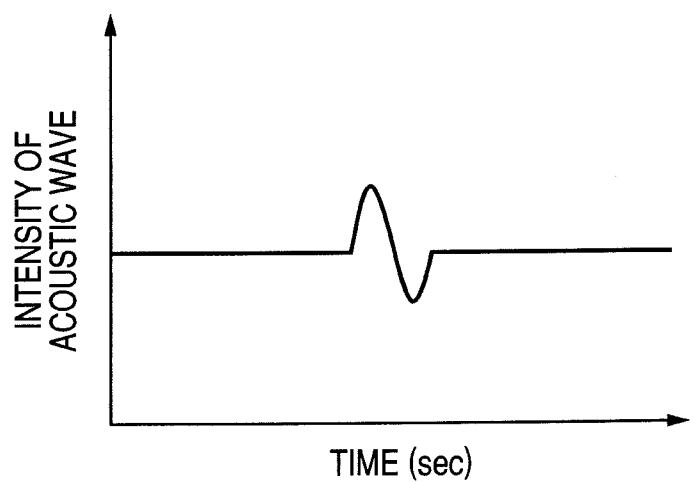

Generally, in a location where the focused ultrasound is not transmitted, an ultrasound signal generated by optical absorption of the optical absorber has an N-shape as in FIG. 2B, with the horizontal axis representing time and the vertical axis represents intensity of ultrasound.

The time width is close to a value obtained by dividing a diameter of the optical absorber by the sound speed.

Figure 2C:
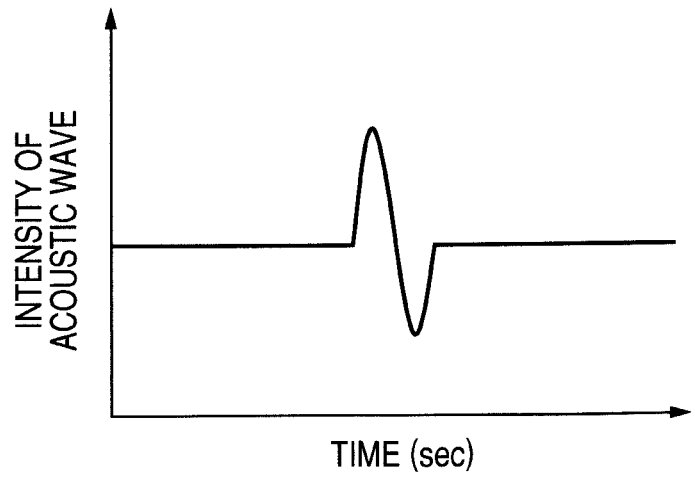

If the phases and periods of the transmitted focused ultrasound in FIG. 2A and the ultrasound generated from the optical absorber in FIG. 2B substantially match each other, the intensity in FIG. 2B is amplified, and an intense signal as in FIG. 2C can be observed.

Thus, a more intense signal than conventional can be observed on the surface of the living body. This is a signal by third ultrasound due to interaction between the ultrasound (second ultrasound) generated from the optical absorber and the focused ultrasound (first ultrasound).

Actually, besides the signal in FIG. 2C, ultrasound signals from other optical absorbers in the living body are also observed.

However, time for arrival of the ultrasound generated from the region where the focused ultrasound is transmitted to can be easily calculated from the sound speed and a distance to the transducer, and thus an ultrasound signal generated form the specific region can be easily identified.

(4) The signal by the third ultrasound obtained in (3) is analyzed to calculate the optical characteristic value of the specific region where the ultrasound is focused into. For example, a characteristic value relating to the optical energy absorption density value or the optical absorption coefficient is calculated. For example, signals can be added based on a delay time corresponding to the specific region where the sound wave is focused into and the distance of all the ultrasound detection elements. Generally, this addition is referred to as delay and sum.

(5) Steps (1) to (4) as a first step are repeated in a second step with the region where the ultrasound is focused into being changed to determine the optical energy absorption density value distribution of the characteristic in the region in the living body or characteristic value distribution relating to the optical absorption coefficient. Specifically, the specific region can be scanned in the subject to repeat measurement to calculate a three-dimensional optical characteristic value distribution in the subject.

The similar processing can be performed with various light wavelengths to image concentration distribution of substances that constitute the living tissue (such as glucose, collagen, oxygenated and reduced hemoglobin and microcalcification area).

The method for determining the optical energy absorption density value distribution in the living body or the characteristic value distribution relating to the optical absorption coefficient is herein used based on the above described flowchart, but the present invention is not limited to the flowchart.

The present invention is essentially directed to generate a more intense photoacoustic signal than the signal generated conventionally by resonance of ultrasound due to the interaction between the ultrasound focused into the specific region and the photoacoustic wave generated from the region, and analyze the signal to obtain information on the optical characteristic value distribution in the living body.

Thus, the present invention is not limited to the flowchart described above.

The condition for effective resonance between the photoacoustic wave and the focused ultrasound will be described hereinafter. For effective resonance therebetween, the phases and frequencies of the first and second ultrasound can be matched.

First, the phase will be described. The position of the specific region into which the focused ultrasound (first ultrasound) is focused is known, and thus the focused ultrasound in the specific region can easily have the same phase as the photoacoustic wave (second ultrasound) generated from the specific region.

Next, the frequency will be described. The frequency of the photoacoustic wave is an inverse of a time width t of the N-shape in FIG. 2B. The time width t can be calculated from a diameter d of the optical absorber/sound speed c for a spherical optical absorber. Thus, when the frequency of the focused ultrasound in FIG. 2A is to be matched with the frequency of the photoacoustic wave, the frequency can be about an inverse of the diameter d of the optical absorber/the sound speed c.

When the size of the optical absorber is unknown, the frequencies cannot be accurately matched. Thus, the frequency of the focused ultrasound can be continuously changed within a specific range. The specific range is about 0.5 to 10 MHz, and can be about 1 to 4 MHz. This can find the condition for effective resonance. In other words, the frequency (or wavelength) of the focused ultrasound emitted to the specific region can be scanned to accommodate the case where the size of the optical absorber is unknown.

Embodiment 2

Next, a biological information imaging apparatus according to Embodiment 2 of the present invention will be described.

Figure 4:
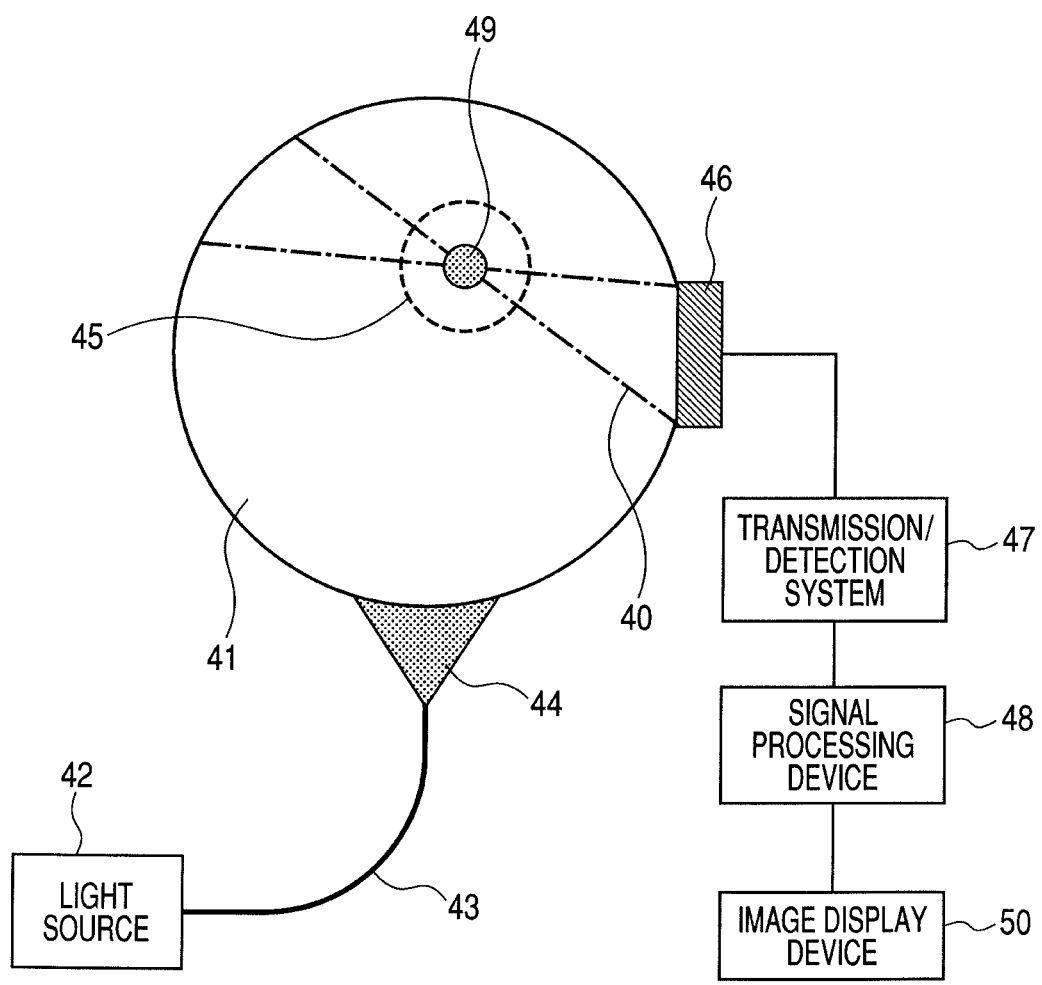
FIG. 4 illustrates an exemplary construction of a biological information imaging apparatus according to Embodiment 2 of the present invention.

FIG. 4 illustrates an exemplary construction of the biological information imaging apparatus according to the embodiment.

The biological information imaging apparatus of the embodiment can image distribution information of a molecular probe introduced into a living body for diagnosing tumor or various diseases labeled by the molecular probe such as Alzheimer's Disease or carotid plaque.

The biological information imaging apparatus of the embodiment includes a light source 42 that irradiates a living body 41 with pulsed light 44 as illustrated in FIG. 4.

The light source 42 emits pulsed light, and includes an optical waveguide 43 for guiding light to a surface of the living body.

The biological information imaging apparatus of the embodiment also includes an ultrasound transmission/detection device 46 having both an ultrasound detection function and an ultrasound transmission function.

Specifically, the biological information imaging apparatus includes an ultrasound transmission/detection device 46 including both functions of an ultrasound transmission device that can focus sound wave into a specific region in the living body, and an acoustic wave detection device that detects a reflection echo or ultrasound 45 generated from an optical absorber in the living body that absorbs a part of energy of the light, the optical absorber being molecular probes 49 integrated in the living body.

Figure 5A:
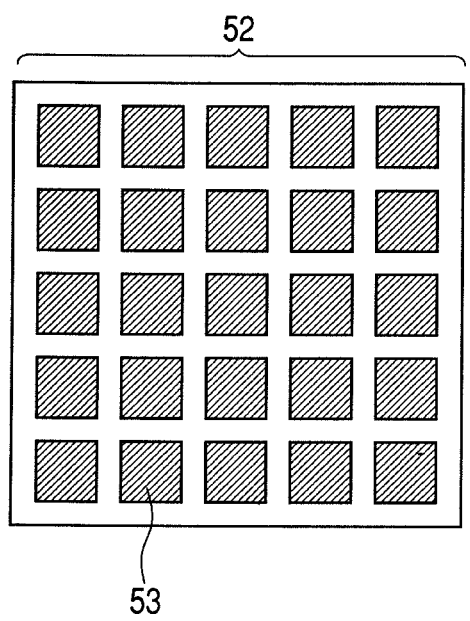
FIGS. 5A and 5B illustrate examples of an ultrasound transmission/detection device used in the biological information imaging apparatus of the present invention.

One example of the ultrasound transmission/detection device includes, for example, one ultrasound transmission/detection element 53 having two functions of an ultrasound transmission element and a sound wave detection element, the elements being arranged on an ultrasound transmission/detection device 52 in the form of a two-dimensional array as illustrated in FIG. 5A.

Figure 5B:
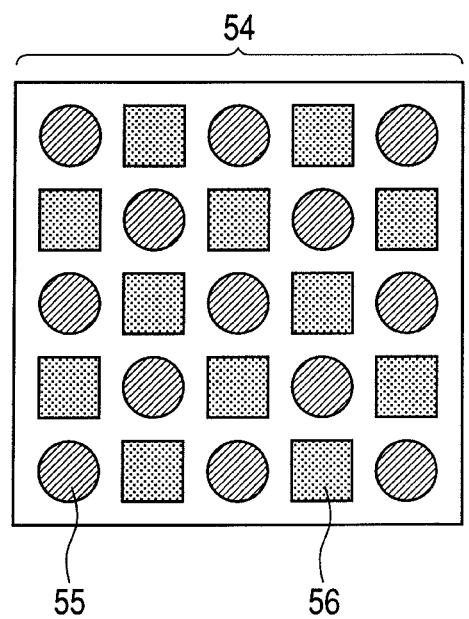

Alternatively, another example of the ultrasound transmission/detection device includes an ultrasound transmission element 55 and an ultrasound detection element 56, the elements being arranged on an ultrasound transmission/detection device 54 in the form of a two-dimensional array as illustrated in FIG. 5B.

The two-dimensionally arranged elements can be used to efficiently obtain an ultrasound signal, but the same advantage can be obtained with a one-dimensional array or only one focused transducer rather than the array. In use of one focused transducer, a focused region of ultrasound can be changed by scanning with the transducer.

Generally, the ultrasound transmission/detection device 46 can be controlled by a transmission/detection system 47 that generates a control signal for generating focused ultrasound, and the generated sound wave can be electronically controlled so as to have an energy density peak in a specific region in the living body.

In the illustrated example, ultrasound is focused into the region where the molecular probe 49 exists in the living body, but ultrasound can be focused into arbitrary locations to some extent.

The signal obtained form the ultrasound transmission/detection device 46 is subjected to signal amplification and analog/digital conversion by the transmission/detection system, and then transmitted to an information processing device 48 that analyzes the signal, and converted into image information based on optical characteristic information of the subject. The image information is imaged by an image display device 50. The same image display device 50 as in Embodiment 1 can be used.

The light source in FIG. 4 emits pulsed light having a particular wavelength absorbed by the molecular probe 49 introduced into the living body.

The light source can be a laser that can generate pulsed light on the order of several to several hundred nanoseconds, and the same light source as in Embodiment 1 can be used.

As the molecular probe 49, indocyanine green (ICG) or gold nanorod is typically used, but any substance may be used that efficiently absorbs light by irradiation with pulsed light and thus generates ultrasound.

The biological information imaging apparatus described in the embodiment can be used to image optical characteristic distribution of the molecular probe introduced into a deep part of the living body as compared with the conventional technique.

Next, a method for analyzing biological information by the signal obtained from the biological information imaging apparatus in the embodiment will be described.

With reference to FIG. 4, an example of a flowchart for obtaining information on optical energy absorption density distribution in the living body or absorption coefficient distribution that can be obtained in Embodiment 2 of the present invention will be described.

(1) The ultrasound transmission/detection device 46 transmits focused ultrasound 40 which has an energy peak at a specific location.

Figure 6A:
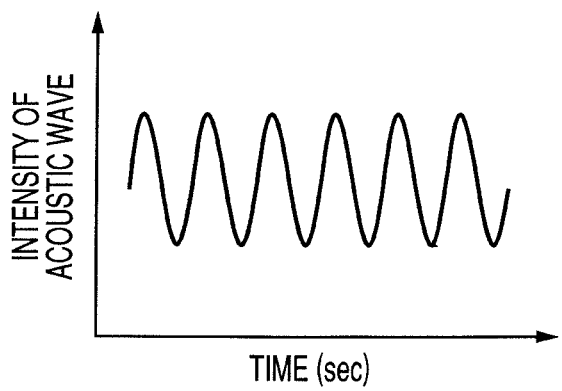
FIGS. 6A, 6B, 6C and 6D illustrate examples of ultrasound signals detected in the biological information imaging apparatus according to Embodiment 2 of the present invention.

For example, an ultrasound signal as in FIG. 6A is applied to a specific region.

In this case, the frequency of the sound wave in FIG. 6A can be about an inverse of a value obtained by dividing the size of the optical absorber in the specific region by sound speed, but the frequency can be continuously changed in a specific range.

FIG. 6A illustrates a waveform of the focused ultrasound having a single frequency, but not limited to this, waveforms of various shapes can be used. Specifically, the waveform of the ultrasound can have a plurality of frequencies after Fourier transform of the waveform rather than having a single frequency. The waveform of the ultrasound having a plurality of frequencies can be used to generate a waveform having a more similar shape to the waveform of the ultrasound generated by optical absorption.

(2) The light source 42 irradiates the surface of the living body with the pulsed light 44.

(3) The ultrasound transmission/detection device 46 detects ultrasound 45 generated from the specific region where the ultrasound is focused into, among the ultrasound generated from the optical absorber (herein molecular probe 49) in the living body that absorbs a part of the energy of the pulsed light 44 from the light source 42 to the living body 41, and converts the ultrasound into an electric signal.

Figure 6B:
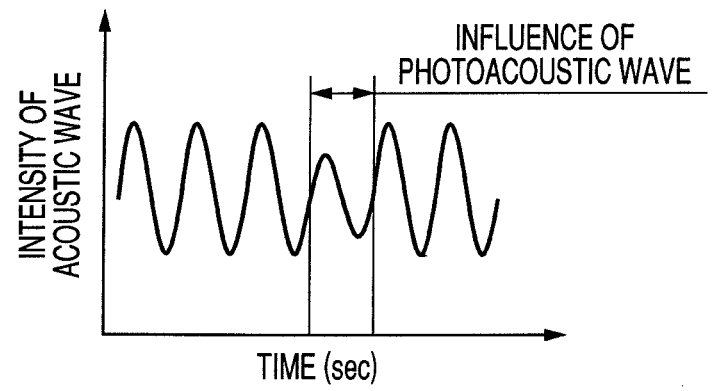
Figure 6C:
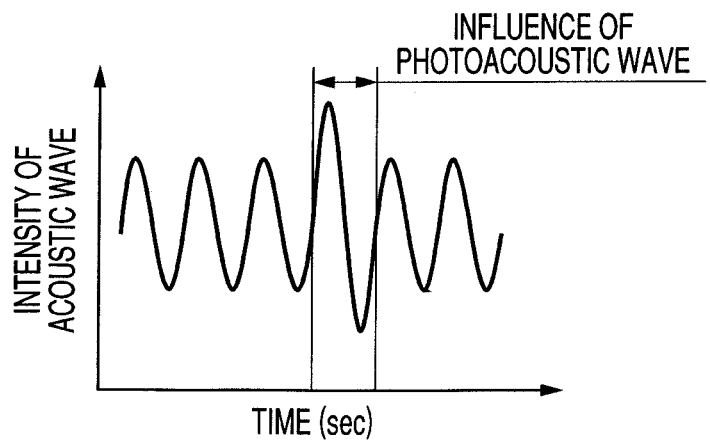

At this time, a reflected wave of transmitted ultrasound overlaps the ultrasound 45 generated from the optical absorber, and thus an ultrasound signal observed by the ultrasound transmission/detection device is, for example, as illustrated in FIG. 6B or 6C. FIG. 6B or 6C illustrates a signal by third ultrasound due to interaction between ultrasound (second ultrasound) generated from the optical absorber and the focused ultrasound (first ultrasound).

Specifically, when the phases and frequencies of the ultrasound generated from the optical absorber in the region where the ultrasound is focused into and the reflection ultrasound (echo) match each other, both are resonated to amplify the intensity of a part of the echo signal as illustrated in FIG. 6C.

When the phases and frequencies of the ultrasound generated from the optical absorber and the echo do not match each other, the intensity of a time region of a part of the echo signal is modulated as illustrated in FIG. 6B.

Ultrasound from other optical absorbers in the living body also exerts an influence on the reflection echo signal, but a propagation time of the ultrasound generated from the region where the ultrasound is focused into can be easily calculated, and the time region can be easily identified from the signal in FIG. 6B or 6C.

(4) The signal by the third ultrasound obtained in (3) is analyzed to calculate an optical characteristic value in the specific region where the ultrasound is focused into. For example, a characteristic value relating to the optical energy absorption density value or the optical absorption coefficient is calculated.

For example, a difference is taken between the reflection echo signal (corresponding to the signal by the focused ultrasound as the first ultrasound) from the ultrasound focused region observed before irradiation with the pulsed light and the ultrasound signal (the signal by the third ultrasound) observed after irradiation with the light.

Figure 6D:
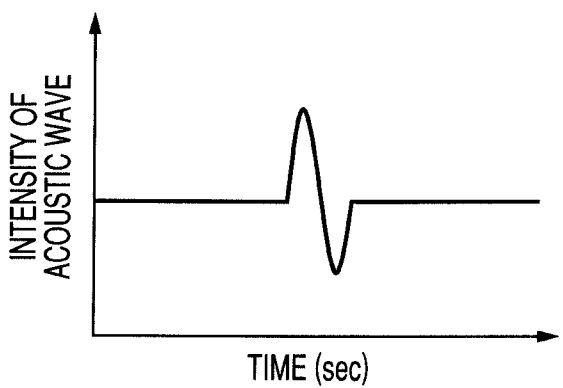

Thus, a signal as illustrated in FIG. 6D can be obtained in which stationary noise is removed from the ultrasound signal (the signal by the second ultrasound) generated from the optical absorber in the specific region where the ultrasound is focused into. The signal is analyzed to calculate the optical energy absorption density value of the specific region where the ultrasound is focused into, or the characteristic value relating to the optical absorption coefficient.

The difference can be thus taken to obtain the signal from which regularly generated noise (stationary noise) is removed. Thus, a signal-to-noise ratio (S/N ratio) can be increased as compared with general measurement.

(5) The above described (1) to (4) are repeated to change the ultrasound focused region to determine the optical energy absorption density value distribution in the living body or the characteristic value distribution relating to the optical absorption coefficient.

The similar processing can be performed with various light wavelengths to image concentration distribution of substances that constitute the living tissue (such as glucose, collagen, oxygenated and reduced hemoglobin and microcalcification area).

The method for determining the optical energy absorption density value distribution in the living body or the characteristic value distribution relating to the optical absorption coefficient is herein used based on the above described flowchart, but the present invention is not limited to the flowchart.

The present invention is essentially directed to obtain a photoacoustic signal having a higher signal-to-noise ratio than conventional from the difference between the ultrasound synthesized signal due to the interaction between the ultrasound focused into the specific region and the photoacoustic wave generated from the region, and the echo signal when the light is not emitted, and analyze the signal to obtain information on the optical characteristic value distribution in the living body.

Thus, the present invention is not limited to the flowchart described above.

EXAMPLE

Next, an exemplary construction of the biological information imaging apparatus according to the example of the present invention will be described.

An exemplary construction of the biological information imaging apparatus that obtains information image relating to distribution of an optical absorber in a living body will be described with reference to FIG. 1.

Since imaging of the actual living body is difficult, the case of imaging a phantom that mimics the living body will be described. The phantom used is 1% of intralipid solidified with agar into a square shape, into which India ink solidified with agar into a spherical shape is inserted as an optical absorber.

As a light source 4, a Q switch Nd:YAG laser that can emit nanosecond pulsed light of 1064 nm is used.

A pulsed width is about 5 nanoseconds, and a repetition speed is 10 Hz. For example, energy of 1 pulsed light is 120 mJ.

The pulsed light is guided to a surface of a living body phantom using a dielectric reflection mirror. The pulsed light is expanded to a region of around 10 $cm^2$ by a beam expander, and exposed to the surface of the living body phantom. Thus, energy of the pulsed light applied to the phantom is about 12 $mJ/cm^2$. An optical fiber or the like is not herein used as an optical waveguide 3, and the light is propagated in air.

The ultrasound transmission device 10 used includes piezoelectric transducers. A total of 324 transducers are arranged in the form of an array of 18 columns and 18 rows, and ultrasound generated from the transducers is controlled by a transmission system 11. The ultrasound transmission device 10 and the transmission system 11 are used to focus ultrasound having a frequency of 5 MHz into a region where the optical absorber which is placed inside the phantom exists.

An observed echo signal from the optical absorber before irradiation has substantially the same frequency as the transmitted ultrasound signal.

Next, the ultrasound signal after the irradiation is ultrasound generated by optical absorption of the optical absorber and the echo signal overlapping each other, and a difference between ultrasound signals measured before and after the irradiation can be taken to reconstruct only the ultrasound signal generated by the optical absorption of the optical absorber in the region where the ultrasound is focused into.

Further, the region where the ultrasound is focused into can be scanned to scan the entire phantom, and thus ultrasound generated by optical absorption of the entire phantom can be measured with high sensitivity.

Further, the signals are transmitted to a computer and analyzed to calculate an optical absorption energy density value of the optical absorber in the region where the ultrasound is focused into, and enable display of an optical absorption energy density distribution image.

Such an apparatus can be used to image optical absorption energy density value distribution of the entire phantom, and enable imaging of an optical absorber in a deeper part from a light irradiation surface as compared with the case without the focused ultrasound.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2008-026067, filed Feb. 6, 2008, which is hereby incorporated by reference herein in its entirety.

The invention claimed is:

1. An apparatus that detects ultrasound comprising:
 a light source configured to irradiate a subject with light;
 an ultrasound transmission unit configured to transmit a
  first focused ultrasound to a specific region in the subject while the subject is not irradiated with the light from said light source and a second focused ultrasound to the specific region while the subject is irradiated with the light from said light source;

an ultrasound detection unit configured to detect a reflection ultrasound or a transmission ultrasound of the first focused ultrasound and to output a signal in response to said detection, wherein said ultrasound detection unit is further configured to detect an overlapped ultrasound in which a photoacoustic wave generated by irradiating the subject with the light and a reflection ultrasound or a transmission ultrasound of the second focused ultrasound are overlapped and to further output an overlapped ultrasound signal in response to said detection of said overlapped ultrasound; and a signal processing unit configured to obtain a difference signal corresponding to an intensity difference between intensity of the overlapped ultrasound signal and intensity of the signal.

2. The apparatus according to claim 1, wherein said ultrasound detection unit and said ultrasound transmission unit form an ultrasound transmission/detection unit, wherein said ultrasound transmission/detection unit is configured to transmit the first and second focused ultrasounds, and wherein said ultrasound transmission/detection unit is configured to detect the reflection ultrasound of the first focused ultrasound.

3. The apparatus according to claim 1, wherein said ultrasound detection unit or said ultrasound transmission unit includes a plurality of ultrasound transducers arranged two-dimensionally.

4. The apparatus according to claim 1, wherein said ultrasound transmission unit or said ultrasound detection unit includes capacitance transducers.

5. The apparatus according to claim 1, wherein said ultrasound detection unit is arranged in a region including a surface of the subject.

6. The apparatus according to claim 1, wherein said light source is a pulsed-light source that outputs pulsed light.

7. The apparatus according to claim 6, wherein said pulsed-light source outputs the pulsed light having a wavelength of 400 nm to 1600 nm.

8. The apparatus according to claim 6, wherein a time width of the pulsed light is 100 picoseconds to 500 nanoseconds.

9. The apparatus according to claim 1, wherein the signal processing unit is configured to obtain information on an optical property value of the specific region based on the difference signal.

10. The apparatus according to claim 1, wherein said ultrasound transmission unit is configured to transmit the first focused ultrasound such that a frequency of the first focused ultrasound is continuously changed.

11. The apparatus according to claim 1, wherein said ultrasound transmission unit is configured to transmit the first and second focused ultrasounds such that waveforms of the first and second focused ultrasounds have a plurality of frequencies.

12. A method comprising the steps of:
transmitting a first focused ultrasound to a specific region in a subject while the subject is not irradiated with light from a light source;

detecting a reflection ultrasound or a transmission ultrasound of the first focused ultrasound and outputting a signal in response to said detection;

irradiating the subject with the light;

transmitting a second focused ultrasound to the specific region in the subject while the subject is irradiated with the light;

detecting an overlapped ultrasound in which a photoacoustic wave generated by irradiating the subject with the light and a reflection ultrasound or a transmission ultrasound of the second focused ultrasound are overlapped and outputting an overlapped ultrasound signal in response to said detection of said overlapped ultrasound; and obtaining a difference signal corresponding to an intensity difference between intensity of the overlapped ultrasound signal and intensity of the signal.

13. The method for detecting ultrasound according to claim 12, wherein the light is pulsed light.

14. The method for detecting ultrasound according to claim 13, wherein a time width of the pulsed light is 100 picoseconds to 500 nanoseconds.

15. The method for detecting ultrasound according to claim 12, wherein a frequency of the second focused ultrasound is continuously changed.

16. The method for detecting ultrasound according to claim 12, further comprising obtaining information on an optical characteristic value of the specific region based on the difference signal.

17. The method for detecting ultrasound according to claim 12, wherein the specific region is scanned in the subject to repeat measurement to obtain a three-dimensional optical characteristic value distribution in the subject.

18. The method for detecting ultrasound according to claim 12, wherein waveforms of the first and second focused ultrasounds have a plurality of frequencies.

* * * * *